United States Patent [19]

Fuyama et al.

[11] 4,303,640
[45] Dec. 1, 1981

[54] OIL-IN-WATER ORGANOPHOSPHORUS INSECTICIDAL EMULSION

[75] Inventors: Hiroshi Fuyama, Toyonaka; Kozo Tsuji, Takatsuki, both of Japan

[73] Assignee: Sumitomo Chemical Company, Ltd., Osaka, Japan

[21] Appl. No.: 130,683

[22] Filed: Mar. 17, 1980

[30] Foreign Application Priority Data

Mar. 16, 1979 [JP] Japan .................... 54-31566

[51] Int. Cl.³ .............. A01N 57/00; A01N 57/26
[52] U.S. Cl. ............................... 424/78; 424/81; 424/168; 424/200; 424/210; 424/212; 424/213; 424/218; 424/362; 424/363
[58] Field of Search ............ 424/78, 81, 200, 213, 424/210, 218, 168

[56] References Cited

U.S. PATENT DOCUMENTS 4,071,617  1/1978  Graves et al. ................. 424/78

OTHER PUBLICATIONS

Chemical Abstracts 81:22286x (1974).
Chemical Abstracts 83:54612h (1975).

*Primary Examiner*—Leonard Schenkman
*Attorney, Agent, or Firm*—Sughrue, Mion, Zinn, Macpeak and Seas

[57] ABSTRACT

An oil-in-water insecticidal emulsion comprising 1 to 50% by weight of as an insecticidally active liquid ingredient at least one organophosphorus compound having a water-solubility of 1,000 ppm or less at a temperature of 10° C.; 2 to 10% by weight of polyvinyl alcohol or gum arabic; and an appropriate amount of a thickener with the balance being water.

7 Claims, No Drawings

OIL-IN-WATER ORGANOPHOSPHORUS INSECTICIDAL EMULSION

BACKGROUND OF THE INVENTION

1. Field of the Invention

This invention relates to a novel oil-in-water insecticidal emulsion (generally called an "aqueous flowable formulation"), which comprises as an insecticidally active liquid ingredient 1 to 50% by weight of at least one organophosphorus compound having a water-solubility of 1,000 ppm or less at a temperature of 10° C.; 2 to 10% by weight of polyvinyl alcohol or gum arabic; and an appropriate amount of a thickener with the balance being water. The insecticidal emulsion of the invention exhibits an insecticidal and acaricidal activity equivalent to a conventional formulation and at the same time it is stable and easier to use.

2 Description of the Prior Art

Of conventionally employed pesticidal formulations in a liquid form, an emulsifiable concentrate which generally consists of a pesticidally active ingredient, a synthetic surfactant and a large amount of an organic solvent often has defects derived from the organic solvent contained therein, such as flammability or malodor, toxicity or irritation to humans, cattle or other domestic animals or poultry, phytotoxicity against crops, and the like.

A wettable powder which does not use an organic solvent is also not fully satisfactory because a spray liquid cannot readily be prepared due to dustiness of its fine powder and aerial low volume application in high concentration (less than 300 ml per 10 ares) is impossible.

For these reasons, studies have been made on aqueous flowable formulations of pesticides and transparent emulsions which replace the organic solvent or powder carrier with water to suspend or disperse fine particles of a hydrophobic pesticidally active ingredient.

Since such aqueous flowable formulations and transparent emulsions are handled in a liquid form, a spray liquid can be prepared without producing dust; and measuring the volume, dilution and other necessary operations can be achieved as easily as with conventional liquid type formulations. In addition, it is accompanied by few or none of the problems of an organic solvent which is toxic or irritating to humans, cattle or other domestic animals or poultry, as well as causes phytotoxicity against crops. However, most aqueous flowable formulations of pesticides hitherto proposed are suspensions using a solid hydrophobic pesticidally active ingredient (such as those disclosed in Japanese Patent Application (OPI) Nos. 126635/74, 76236/75 and 148625/77 (the term "OPI" as used herein refers to a "published unexamined Japanese patent application"), and U.S. Pat. No. 4,071,617), and no practical oil-in-water emulsion that uses a pesticidally active ingredient in an oil form has yet been developed due to difficulties in stabilizing its physical properties over an extended period of time.

Transparent emulsions used as oil-in-water pesticidal compositions are disclosed in Japanese Pat. Publication No. 20520/71, and Japanese patent application (OPI) Nos. 54547/74 and 122628/77, but these transparent emulsions are a water-soluble type that uses a large quantity of a general-purpose synthetic surfactant to reduce the particle size of the pesticidally active ingredient to less than $0.1\mu$, and no satisfactory technique has been proposed to solve the cost and toxicity problems which accompany the use of large quantities of surfactant.

SUMMARY OF THE INVENTION

Various studies have been directed to a method of producing an oil-in-water insecticidal emulsion which contains an organophosphorus compound having a water-solubility of 1,000 ppm or less at a temperature of 10° C. as an active liquid ingredient and which retains its chemical and physical properties for an extended period of time and is able to exhibit an insecticidal effect comparable to the above-described conventional formulations but which, unlike the conventional formulations, does not employ an organic solvent or a general-purpose synthetic surfactant such as a higher alcohol sulfate, a higher alcohol sulfonate, an alkyl sulfonate, an aryl sulfonate, an alkyl aryl sulfonate or a formalin condensate thereof, a fatty acid ester compound, a polyoxyethylene alkyl ether, a polyoxyethylene aryl ether, a polyoxyethylene alkyl aryl ether, a polyoxyethylene phenyl phenol derivative or a polyoxyethylene sorbitan alkylate and the like. As a result of these studies, the present inventors have found that polyvinyl alcohol or gum arabic is the most suitable dispersing agent for organophosphorus compounds having a water-solubility of 1,000 ppm or less at a temperature of 10° C. as an insecticidally active liquid ingredient.

Accordingly, it is a principal object of the present invention to provide an insecticidally active oil-in-water emulsion which retains its physical and chemical properties for an extended period of time.

More particularly, it is an object of the present invention to provide an insecticidally active oil-in-water emulsion which is free from the drawbacks which accompany the conventional use of general-purpose synthetic surfactants and organic solvents.

It is another object of the present invention to provide an insecticidally active oil-in-water emulsion containing at least one organophosphorus compound having a water-solubility of 1,000 ppm or less at a temperature of 10° C. (hereinafter sometimes referred to as "organophosphorus compound") and a method for the preparation thereof.

DETAILED DESCRIPTION OF THE INVENTION

An insecticidal emulsion that meets the requirements described above can be economically prepared by a simple method which comprises dispersing by mechanical means fine particles (or fine droplets) of an organophosphorus compound in an aqueous solution of polyvinyl alcohol or gum arabic and adding a suitable thickener to stabilize the suspended fine particles of the compound.

A brief description of the method of producing the oil-in-water insecticidal emulsion of this invention will be given below. First, an insecticidally active liquid ingredient of the organophosphorus compound is added to a 2 to 20 wt% aqueous solution of polyvinyl alcohol or gum arabic, and a conventonal stirrer such as a T.K. Homomixer (a homogenizer manufactured by Tokushu Kika Kogyo Co., Ltd.) or a Shinagawa All-Purpose Mixer (a mixer manufactured by San-Ei-Seisakusho, Ltd.) is used to disperse the particles of the active ingredient (A.I.), generally at ambient temperature or, if necessary, at an elevated temperature (about 40° to 80°

C.). The size of the emulsified particles of the active ingredient can be varied wihtin the range of from about 1 to 200μ depending upon the stirring force or the content of polyvinyl alcohol or gum arabic. A microscope is used to check the size of the emulsified particles of the active ingredient. Finally, for the purpose of preventing settling of the emulsified particles and improving the dispersion stability, an aqueous solution of a thickener is added to the emulsion in a suitable amount. The resulting oil-in-water insecticidal emulsion remains stable for an extended period.

While typical examples of organophosphorus compounds which can be used in the present invention are hereunder given, it is to be understood that they are by no means meant to limit the scope of this invention. Representative examples include:

O,O-dimethyl O-(3-methyl-4-nitrophenyl)phosphorothioate (general name, fenitrothion; hereinafter referred to "Compound (1);" water-solubility at 10° C., 5 ppm), O,O-dimethyl S-[1,2-di-(ethoxycarbonyl)ethyl]-phosphorodithioate (general name, malathion; hereinafter referred to "Compound (2);" water-solubility at 10° C., 145 ppm), O,O-dimethyl O-(4-cyanophenyl)phosphorothioate (Cyanox, a trade name of Sumitomo Chemical Company, Limited, Japan; hereinafter referred to "Compound (3);" water-solubility at 10° C., 28 ppm), 0,0-dimethyl S-[α-(ethoxycarbonyl)benzyl]-phosphorodithioate (general name, cidial; hereinafter referred to "Compound (4);" water-solubility at 10° C., 4 ppm), and O,O-dimethyl O-(2-isopropyl-4-methyl-6-pyrimidinyl)-phosphorothioate (general name, diazinon; hereinafter referred to "Compound (5);" water-solubility at 10° C., 50 ppm).

A suitable example of the polyvinyl alcohol that can be used in this invention has a degree of polymerization less than about 1,500 and a degree of hydrolysis between about 70 to 90 mol%. One such example is Gohsenol GL-05 (polyvinyl alcohol manufactured by The Nippon Synthetic Chemical Industry Co., Ltd. having a degree of polymerization of less than 1,000 and a degree of hydrolysis of from 86.5 to 89 mol%).

Examples of the thickener that can be used in this invention include tragacanth gum, guar gum, sodium alginate, sodium carboxymethyl cellulose, sodium carboxy-methyl starch, hydroxyethyl cellulose, methyl cellulose, polyacrylic acid or derivatives thereof, etc. Commercially available thickeners include Agrisol FL-100F (aqueous solution containing polyacrylic acid and sorbitol, a product of Kao-Atlas Co., Ltd.), Primal ASE-60 (an acid-type (containing carboxyl groups at terminal ends and side chains) acryl emulsion, a product of Japan Acrylic Chemical Co., Ltd.), Rheogic 250H (sodium polyacrylate, a product of Nihon Junyaku Co., Ltd.) and Carbopol (a carboxyvinyl polymer of high polymerization degree, a product of The B. F. Goodrich Company). These thickeners are used in an amount within the range of from 0.1 to 20 wt%, and the optimum amount of addition varies from thickener to thickener.

Since the oil-in-water insecticidal emulsion of this invention contains no organic solvent, it is free from potential hazards such as flammability and malodor of an organic solvent and its toxicity or irritation to humans, cattle or other domestic animals or poultry, or phytotoxicity against crops. In addition, because of high miscibility with water used as a diluent for preparation of a spray liquid, measuring the volume, dilution and other necessary operations can be performed with ease which is comparable to the case of the conventional liquid type formulations.

This invention will hereunder be described in greater detail by reference to the following Examples which are given here for illustrative purposes only and are by no means intended to limit the scope of this invention.

EXAMPLE 1

10 g of each of Compounds (1), (2), (3), (4) and (5) was added to 40 g of a 10 wt% aqueous solution of Gohsenol GL-05, and the mixture was stirred at ambient temperature with a T.K. Homomixer at 5,000 ppm for a period of 5 minutes.

To the mixture was added 50 g of a neutralized 20 wt% aqueous solution of Agrisol FL-100F at ambient temperature, and the resultant mixture was lightly stirred for a few minutes to obtain 100 g of a homogeneous oil-in-water insecticidal emulsion containing 10 wt% of the active ingredient. The particles of the emulsified active ingredient were in the range of from 1 to 40μ in size.

EXAMPLE 2

40 g of Compound (1) was added to 50 g of a 10 wt% aqueous solution of Gohsenol GL-05, and the mixture was stirred at ambient temperature with a T.K. Homomixer at 5,000 rpm for a period of 5 minutes.

To the mixture was added 10 g of neutralized Agrisol FL-100F at ambient temperature, and the resultant mixture was lightly stirred for a few minutes to obtain 100 g of a homogeneous oil-in-water insecticidal emulsion containing 40 wt% of Compound (1). The particles of the emulsified active ingredient were in the range of from 1 to 40μ in size.

EXAMPLE 3

The procedure of Example 2 was repeated except that the T.K. Homomixer was rotated at 2,500 rpm. The product was 100 g of an oil-in-water insecticidal emulsion containing 40 wt% of Compound (1). The particles of the emulsified active ingredient were in the range of from 1 to 160μ in size.

EXAMPLE 4

Each of Compounds (1) to (5) in an amount indicated in Table 1 below was added to an aqueous solution of Gohsenol GL-05 or gum arabic shown in Table 1, and the mixture was stirred at ambient temperature with a T.K. Homomixer at 5,000 rpm for a period of 5 minutes. To the mixture was added an aqueous solution of the thickener shown in Table 1 at ambient temperature and the resulting mixture was stirred to obtain 100 g of an oil-in-water emulsion in each instance.

TABLE 1

| Active Ingredient and Amount | Gohsenol GL-05 or Aq. Soln. of Gum Arabic | Thickener and Amount | Content of Active Ingredient (% by weight) | Particle Size (μ) |
|---|---|---|---|---|
| Compound (1), 20 g | 10 wt% Aqueous Solution of Gohsenol GL-05, 50 g | 30 wt% Aqueous Solution of Neutralized Agrisol FL-100F, 30 g | 20 | 1 to 30 |
| Compound (2), 40 g | 10 wt% Aqueous Solution of Gohsenol GL-05, 50 g | 8 wt% Aqueous Solution of Sodium Carboxymethyl Cellulose, 10 g | 40 | 1 to 40 |
| Compound (3), 1 g | 10 wt% Aqueous Solution of Gum Arabic, 50 g | 2 wt% Aqueous Solution of Sodium Alginate, 49 g | 1 | 1 to 50 |
| Compound (4), 5 g | 5 wt% Aqueous Solution of Gum Arabic, 80 g | 2 wt% Aqueous Solution of Rheogic 250H, 15 g | 5 | 1 to 50 |
| Compound (5), 10 g | 10 wt% Aqueous Solution of Gohsenol GL-05, 50 g | 25 wt% Aqueous Solution of Neutralized Agrisol FL-100F, 40 g | 10 | 1 to 30 |

EXAMPLE 5

The stability of the composition of this invention was tested using the emulsions obtained in Examples 1 (hereinafter referred to "Composition 1" and "Composition 3," respectively). The results obtained are shown in Table 2 below.

TABLE 2

| Emulsion and Active Ingredient | Storage Conditions | Percent Decomposition of Active Ingredient* | Dispersion Stability |
|---|---|---|---|
| Composition 1 [Compound (1)] | 40° C. | | |
| | 1 month | 0 | Uniform dispersion without settlement of active ingredient |
| | 2 months | 0.3 | Uniform dispersion without settlement of active ingredient |
| | 3 months | 0.7 | Uniform dispersion without settlement of active ingredient |
| | 50° C. | | |
| | 1 month | 0.5 | Uniform dispersion without settlement of active ingredient |
| | 3 months | 2.0 | Uniform dispersion without settlement of active ingredient |
| | At Room Temp. | | |
| | 2 years | 2.0 | Uniform dispersion without settlement of active ingredient |
| Composition 3 [Compound (3)] | 40° C. | | |
| | 1 month | 0.2 | Uniform dispersion without settlement of active ingredient |
| | 2 months | 0.5 | Uniform dispersion without settlement of active ingredient |
| | 3 months | 1.2 | Uniform dispersion without settlement of active ingredient |
| | 50° C. | | |
| | 1 month | 0.8 | Uniform dispersion without settlement of active ingredient |
| | 3 months | 3.5 | Uniform dispersion without settlement of active ingredient |
| | At Room Temp. | | |
| | 2 years | 4.5 | Uniform dispersion without settlement of active ingredient |

*Based on the active ingredient content determined at the time of preparation.

The following experiment was conducted to demonstrate the effectiveness of gum arabic and polyvinyl alcohol as a dispersing agent compared with other water-soluble polymers.

EXPERIMENT 1

180 g of a 2 wt% aqueous solution of each of the following substances was prepared: albumin, cellulose sulfate derivative, sodium alginate, carrageenan, polyvinyl pyrrolidone, carboxymethyl cellulose, sodium lignin sulfonate, gelatin, gum arabic and Gohsenol GL-05. To each of the aqueous solutions was added 20 g of each of the five insecticidally active liquid organo-phosphorus compounds indicated in Table 3 below. A T.K. Homomixer was used to disperse the active ingredients until their emulsified particles were from 1 to 100μ in size, and each of the resulting emulsions was put in a sealable glass container which was stored in a constant temperature dryer at 60° C. for one day, and observed for its dispersion stability. The results of the observation are set forth in Table 3 below.

TABLE 3

Evaluation of Dispersion Stability

| Insecticidal Compound | Albumin | Cellulose Sulfate Derivative | Sodium Alginate | Carrageenan | Polyvinyl Pyrrolidone | Carboxy-methyl Cellulose | Sodium Lignin Sulfonate | Gelatin | Gum Arabic | Gohsenol GL-05 |
|---|---|---|---|---|---|---|---|---|---|---|
| Compound (1) | x | x | x | Δ | x | x | Δ | x | o | o |
| Compound (2) | x | x | x | Δ | x | x | Δ | x | o | o |
| Compound (3) | x | x | x | Δ | x | x | Δ | x | o | o |
| Compound (4) | x | x | x | Δ | x | x | Δ | x | o | o |
| Compound (5) | x | x | x | Δ | x | x | Δ | x | o | o |

Criteria for evaluation of dispersion stability
o: No trace of coalescence of particles of active ingredient.
Δ: Particles of active ingredient coalesced and grew in size, but no separation between oil phase and aqueous phase.
x: Particles of active ingredient coalesced until oil phase separated from aqueous phase.

Table 3 clearly indicates the effectiveness of gum arabic and polyvinyl alcohol as a dispersing agent.

Further, the following experiment was conducted to demonstrate that liquid organophosphorus compounds having a water-solubility of 1,000 ppm or less at 10° C. are suitable as active ingredients to be incorporated into the composition of this invention from the standpoint of dispersion stability.

EXPERIMENT 2

20 parts by weight of each of Compounds (1), (2), (3), (4) and (5) of the present invention as an insecticidally active liquid organophosphorus compound having a water-solubility of 1,000 ppm or less at 10° C., and each of O,O-dimethyl O-(2,2-dichlorovinyl)phosphate (general name, dichlorovos; water-solubility at 10° C., about 10,000 ppm) and O,O-dimethyl 3-cyanophenyl-methylphosphonate (water-solubility at 10° C., about 6,000 ppm) as an insecticidally active liquid organophosphorus compound having a water-solubility higher than 1,000 ppm at 10° C. was added separately to 80 parts by weight of a 2 wt% aqueous solution of Gohsenol GL-05 or 80 parts by weight of a 2 wt% aqueous solution of gum arabic, and the mixture was dispersed using a T.K. Homomixer until the emulsified particles were from 1 to 100μ in size. Each of the resulting emulsions was put in a sealable glass container which was stored in a constant temperature dryer at 50° C. for one day, and observed for its dispersion stability. The results obtained are shown in Table 4 below.

TABLE 4

Evaluation of Dispersion Stability

| Insecticidal Compound (water-solubility at 10° C.) | Aq. Soln. of Gohsenol GL-05 | Aq. Soln. of Gum Arabic |
|---|---|---|
| Compound (1) (5 ppm) | o | o |
| Compound (2) (145 ppm) | o | o |
| Compound (3) (28 ppm) | o | o |
| Compound (4) (4 ppm) | o | o |
| Compound (5) (50 ppm) | o | o |
| O,O-Dimethyl O-(2,2-dichlorovinyl)phosphate (ca. 10,000 ppm) | x | x |
| O,O-Dimethyl 3-cyanophenylmethylphosphonate (ca. 6,000 ppm) | x | x |

Criteria for evaluation of dispersion stability
o: No trace of coalescence of particles of active ingredient.
x: Particles of active ingredient coalesced until oil phase separated from aqueous phase.

As is apparent from the results shown in Table 4 above, the liquid organophosphorus compounds having a water-solubility of 1,000 ppm or less exhibited markedly high dispersion stability and were found suitable as active ingredients to be incorporated into the composition of this invention.

The following experiment was conducted to demonstrate the effectiveness of the oil-in-water insecticidal emulsion prepared by this invention.

EXPERIMENT 3

The five oil-in-water emulsions prepared in Example 1 each containing 10 wt% of Compound (1), (2), (3), (4) and (5) as an active ingredient (hereinafter referred to Composition 1, 2, 3, 4 and 5, respectively) were diluted with water to a concentration of 500 ppm of the active ingredient and each of the solution was applied to pot-planted eggplant (species: Senryo No.2) on a turntable at a rate of 50 ml/3 pots. After drying in air, completely opened leaves thus treated were put in a plastic cup together with a group of 10 adult 28-spotted lady beetles, and the mortality at the end of the second day was recorded.

In this experiment, five Control Formulations 1, 2, 3, 4 and 5 having the following composition, each containing 10 wt% of the same active ingredient as that of Composition 1, 2, 3, 4 and 5 was used as control for the treatment in the same manner as above.

| Control Formulations 1 to 5 | |
|---|---|
| Active Ingredient (Compound 1, 2, 3, 4 or 5) | 10.0 W/W% |
| Sorpol 3005X (a mixture of nonionic surface active agent containing as a major component polyoxyethylene phenyl phenol derivative and organic sulfonate-type anionic surface active agent, Toho Chemical Co., Ltd.) | 10.0 W/W% |
| Xylene | Balance |
| | Total 100.0 |

This test was repeated twice and the results obtained are shown in Table 5 below in terms of average values to two runs.

TABLE 5

| Emulsion/Control Formulation | Percent Mortality of 28-Spotted Lady Beetle (%) |
|---|---|
| Composition 1 | 100 |
| Control Formulation 1 | 100 |
| Composition 2 | 100 |
| Control Formulation 2 | 100 |
| Composition 3 | 100 |
| Control Formulation 3 | 100 |
| Composition 4 | 100 |
| Control Formulation 4 | 100 |
| Composition 5 | 100 |

TABLE 5-continued

| Emulsion/Control Formulation | Percent Mortality of 28-Spotted Lady Beetle (%) |
|---|---|
| Control Formulation 5 | 100 |

As is clear from the above table, all samples of the oil-in-water insecticidal emulsion of this invention proved to have an excellent effect equivalent to the control formulation.

EXPERIMENT 4

Aqueous solutions of Compositions 1, 3, 4 and 5 and Control Formulations 1, 3, 4 and 5 as used in Experiment 3 having a predetermined concentration of the active ingredient (500 ppm and 1,000 ppm) were applied to rice plant at a shooting stage cultivated in a 1/10,000 are Wagner pot on which larvae of rice stem borer immediately after hatching had been encroached, at a rate of 30 ml/2 pots. Five days after application, the rice plant thus treated was disintegrated to determine the mortality of encroached larvae. This test was repeated twice and the results obtained are shown in Table 6 below in terms of average values to two runs.

TABLE 6

| Emulsion/Control Formulation | Percent Mortality of Encroached Larvae of Rice Stem Borer | |
|---|---|---|
|  | 500 ppm | 1,000 ppm |
| Composition 1 | 100 | 100 |
| Control Formulation 1 | 100 | 100 |
| Composition 3 | 100 | 100 |
| Control Formulation 3 | 100 | 100 |
| Composition 4 | 100 | 100 |
| Control Formulation 4 | 100 | 100 |
| Composition 5 | 100 | 100 |
| Control Formulation 5 | 100 | 100 |

As is clear from the above table, all samples of the oil-in-water insecticidal emulsion of this invention proved to have an excellent effect equivalent to the control formulation.

EXPERIMENT 5

To evaluate the irritating effect of the oil-in-water insecticidal emulsion of this invention on mucous membranes, the irritating effect of the emulsion obtained in Example 2 or 4 [Compound (1) or Compound (2) as an active ingredient, respectively] on the eyes of a rabbit was examined in accordance with the Environmental Protection Agency Guideline [Federal Register, 43, 37359–37360 (1978)].

In this test the two oil-in-water insecticidal emulsions each containing 40 wt% of the same active ingredient prepared as described below were also compared as control formulations.

| Control Formulations (40 W/W% Emulsifiable Concentrates) | |
|---|---|
| Control Formulation (1) | |
| Compound (1) | 40 W/W% |
| Sorpol SM-100S (A mixture of nonionic surface active agent containing as a major component polyoxyethylene styryl phenyl ether derivative and organic sulfonate-type anionic surface active agent, Toho Chemical Co., Ltd.) | 15 W/W% |
| Xylene | Balance |
|  | Total 100 |
| Control Formulation (2) | |
| Compound (2) | 40 W/W% |
| Sorpol L550 (A mixture of ether-type nonionic surface active agent and organic sulfonate-type anionic surface active agent, Toho Chemical Co., Ltd.) | 11 W/W% |
| Sorpol H770 (A mixture of ether-type nonionic surface active agent and organic sulfonate-type anionic surface active agent, Toho Chemical Co., Ltd.) | 1 W/W% |
| Epichlorhydrin | 1 W/W% |
| Xylene | Balance |
|  | Total 100 |

The results obtained are shown in Table 7 below, in which the maximum total score of the strength of irritation reaction and the strength of irritation was obtained in accordance with the standard shown in Table 8 below.

TABLE 7

| Emulsion/Control Formulation | Organism |  | Irritation Strength | | | | | | | Maximum Total Point |
|---|---|---|---|---|---|---|---|---|---|---|
|  |  |  | 1 hr | 24 hrs | 48 hrs | 72 hrs | 96 hrs | 7 days | 14 days |  |
| Composition of Present Invention [Compound (1)] | Cornea | Opacity-degree of density | 0 | 0 | 0 | 0 | 0 | 0 |  |  |
|  |  | Area of cornea involved | 0 | 0 | 0 | 0 | 0 | 0 |  |  |
|  | Iris |  | 0 | 0 | 0 | 0 | 0 | 0 |  |  |
|  |  | Redness | 1 | 0 | 0 | 0 | 0 | 0 |  |  |
|  | Conjunctivae | Chemosis | 0 | 0 | 0 | 0 | 0 | 0 |  |  |
|  |  | Discharge | 0 | 0 | 0 | 0 | 0 | 0 |  | 2.0/110 |
| Control Formulation [Compound (1)] | Cornea | Opacity-degree of density | 0 | 1 | 1 | 1 | 1 | 1 | 0 |  |
|  |  | Area of cornea involved | 0 | 4 | 4 | 2–4 | 1–4 | 1–2 | 0 |  |
|  | Iris |  | 1 | 1 | 0 | 0 | 0 | 0 | 0 |  |
|  |  | Redness | 2 | 2 | 2 | 1–2 | 1–2 | 1 | 0 |  |
|  | Conjunctivae | Chemosis | 1–2 | 0 | 0 | 0 | 0 | 0 | 0 |  |
|  |  | Discharge | 0 | 2 | 1–2 | 1–2 | 0–1 | 0 | 0 | 33.0/110 |
| Composition of Present Invention [Compound (2)] | Cornea | Opacity-degree of density | 0 | 0 | 0 | 0 | 0 | 0 |  |  |
|  |  | Area of cornea involved | 0 | 0 | 0 | 0 | 0 | 0 |  |  |
|  | Iris |  | 0 | 0 | 0 | 0 | 0 | 0 |  |  |

TABLE 7-continued

| Emulsion/Control Formulation | | Organism | Irritation Strength | | | | | | | Maximum Total Point |
|---|---|---|---|---|---|---|---|---|---|---|
| | | | 1 hr | 24 hrs | 48 hrs | 72 hrs | 96 hrs | 7 days | 14 days | |
| | | Redness | 1 | 1 | 0 | 0 | 0 | 0 | | |
| | Conjunctivae | Chemosis | 0 | 0 | 0 | 0 | 0 | 0 | | |
| | | Discharge | 0 | 1 | 0 | 0 | 0 | 0 | | 4.0/110 |
| Control Formulation [Compound (2)] | Cornea | Opacity-degree of density | 0 | 1 | 1 | 1 | 1 | 1 | 0 | |
| | | Area of cornea involved | 0 | 4 | 4 | 2–4 | 1–4 | 1–2 | 0 | |
| | Iris | | 1 | 1 | 1 | 1 | 0 | 0 | 0 | |
| | | Redness | 2 | 2 | 2 | 1–2 | 1–2 | 1 | 0 | |
| | Conjunctivae | Chemosis | 3 | 1 | 0 | 0 | 0 | 0 | 0 | |
| | | Discharge | 0 | 1 | 0–1 | 0–1 | 0 | 0 | 0 | 32.3/110 |

TABLE 8
Scale for Scoring Ocular Lesions

1. Cornea
   (A) Opacity - degree of density (area taken for reading)
   - No opacity — 0
   - Scattered or diffuse area - details of iris clearly visible — 1
   - Easily discernible translucent areas, details of iris slightly obscured — 2
   - Opalescent areas, no details of iris visible, size of pupil barely discernible — 3
   - Opaque, iris invisible — 4

(B) Area of cornea involved
   - One quarter (or less) but not zero — 1
   - Greater than one quarter - less than one-half — 2
   - Greater than one-half less than three quarters — 3
   - Greater than three quarters up to whole area — 4

Score equals A × B × 5  Total maximum = 80

2. Iris
   (A) Values
   - Normal — 0
   - Folds above normal, congestion, swelling, circumcorneal injection (any one or all of these or combination of any thereof), iris still reacting to light (sluggish reaction is positive) — 1
   - No reaction to light, hemorrhage; gross destruction (any one or all of these) — 2

Score A × 5  Total possible maximum = 10

3. Conjunctivae
   (A) Redness (refers to palpebral conjunctivae only)
   - Vessels normal — 0
   - Vessels definitely injected above normal — 1
   - More diffuse, deeper crimson red, individual vessels not easily discernible — 2
   - Diffuse beefy red — 3

(B) Chemosis
   - No swelling — 0
   - Any swelling above normal (includes nictitation membrane) — 1
   - Obvious swelling with partial eversion of the lids — 2
   - Swelling with lids about half closed — 3
   - Swelling with lids about half closed to completely closed — 4

(C) Discharge
   - No discharge — 0
   - Any amount different from normal (does not include small amount observed in inner canthus of normal animals) — 1
   - Discharge with moistening of the lids and hairs just adjacent to the lids — 2
   - Discharge with moistening of the lids and considerable area around the eye — 3

Score (A + B + C) × 2  Total maximum = 20

The maximum total score is the sum of all scores obtained for the cornea, iris and conjunctivae.

It was confirmed from Table 7 above that the degree of irritation of the oil-in-water insecticidal emulsion of this invention is weaker than that of the control formulation containing the same active ingredient as that in the emulsion of this invention.

EXPERIMENT 6

The test on acute toxicity was conducted by orally administering a diluted solution of each of the emulsion obtained in Example 4 containing Compound (1) as an active ingredient and the control formulation having the following composition (diluted with distilled water) to groups of dd-strain mice (one group = 10 male mice plus 10 female mice) at a dose of 20 ml/kg per mouse and 2 weeks after the administration, observing the number of dead mice. The results obtained are shown in Table 9 below, in which the $LD_{50}$ value was obtained in accordance with the method proposed by Litchfield and Wilcoxon (see J. Pharmacol. Exptl. Therp., 96, 99 (1949)).

TABLE 9
Acute Oral Toxicity in Mice

| Active Ingredient | Test Composition | $LD_{50}$ (mg/kg) | |
|---|---|---|---|
| | | Male Mice | Female Mice |
| Compound (1) | Emulsion of Present Invention (Example 4) | 2,480 | 3,590 |
| Compound (1) | Control Formulation* | 1,510 | 2,260 |

*20 W/W% Emulsifiable concentrate of Compound (1) having the following formulation.
- Compound (1)     20 W/W%
- Sorpol SM-100S     15 W/W%

TABLE 9-continued

| | Acute Oral Toxicity in Mice | |
|---|---|---|
| Xylene | | Balance |
| | Total | 100 |

As is clear from Table 9 above, the acute oral toxicity in mice of the oil-in-water insecticidal emulsion of this invention was less than that of the control formulation containing the same active ingredient as that in the emulsion of this invention.

While the invention has been described in detail and with reference to specific embodiments thereof, it will be apparent to one skilled in the art that various changes and modifications can be made therein without departing from the spirit and scope thereof.

What is claimed is:

1. An oil-in-water insecticidal emulsion consisting essentially of, as an insecticidally active liquid ingredient 1 to 50% by weight of at least one organophosphorus compound having a water-solubility of 1,000 ppm or less at a temperature of 10° C., 2 to 10% by weight of polyvinyl alcohol or gum arabic and 0.1 to 20% by weight of a thickener selected from the group consisting of tragacanth gum, guar gum, sodium alginate, sodium carboxymethyl cellulose, sodium carboxymethyl starch, hydroxyethyl cellulose, methyl cellulose and a polyacrylic acid or a derivative thereof with the balance being water.

2. The oil-in-water insecticidal emulsion of claim 1, wherein said organophosphorus compound is O,O-dimethyl O-(3-methyl-4-nitrophenyl)-phosphorothioate.

3. The oil-in-water insecticidal emulsion of claim 1, wherein said organophosphorus compound is O,O-dimethyl S-[1,2-di-(ethoxycarbonyl)ehtyl]-phosphorodithioate.

4. The oil-in-water insecticidal emulsion of claim 1, wherein said organophosphorus compound is O,O-dimethyl O-(4-cyanophenyl)phosphorothioate.

5. The oil-in-water insecticidal emulsion of claim 1, wherein said organophosphorus compound is O,O-dimethyl S-[α-(ethoxycarbonyl)benzyl]-phosphorodithioate.

6. The oil-in-water insecticidal emulsion of claim 1, wherein said organophosphorus compound is O,O-dimethyl O-(2-isopropyl-4methyl-6-pyrimidinyl)phosphorothioate.

7. A method for killing insects which comprises applying to the insects an insecticidally effective amount of the oil-in-water insecticidal emulsion of claim 1.

* * * * *